(12) United States Patent
Maack

(10) Patent No.: US 9,905,003 B2
(45) Date of Patent: Feb. 27, 2018

(54) PROCESSING DUAL ENERGY SPECTRAL MAMMOGRAPHY IMAGES

(71) Applicant: KONINKLIJKE PHILIPS N.V., Eindhoven (NL)

(72) Inventor: Hanns-Ingo Maack, Norderstedt (DE)

(73) Assignee: Koninklijke Philips N.V., Eindhoven (NL)

( * ) Notice: Subject to any disclaimer, the term of this patent is extended or adjusted under 35 U.S.C. 154(b) by 68 days.

(21) Appl. No.: 15/035,581

(22) PCT Filed: Nov. 12, 2014

(86) PCT No.: PCT/EP2014/074298
§ 371 (c)(1),
(2) Date: May 10, 2016

(87) PCT Pub. No.: WO2015/074916
PCT Pub. Date: May 28, 2015

(65) Prior Publication Data
US 2016/0267651 A1  Sep. 15, 2016

(30) Foreign Application Priority Data
Nov. 20, 2013  (EP) .................................... 13193661

(51) Int. Cl.
*G06K 9/00*  (2006.01)
*G06T 7/00*  (2017.01)
(Continued)

(52) U.S. Cl.
CPC ............ *G06T 7/0012* (2013.01); *A61B 6/482* (2013.01); *A61B 6/5258* (2013.01);
(Continued)

(58) Field of Classification Search
CPC .... G06T 5/50; G06T 5/10; G06T 5/20; G06T 5/40; G06T 5/3205; G06T 5/325;
(Continued)

(56) References Cited

U.S. PATENT DOCUMENTS 4,542,459 A * 9/1985 Riederer ............... H04N 5/3205
                                                    348/E5.089
5,771,269 A * 6/1998 Chao ........................ A61B 6/06
                                                    378/147
(Continued)

FOREIGN PATENT DOCUMENTS

WO  2008/084880  7/2008
WO  2013/076662  5/2013

OTHER PUBLICATIONS

Dahlman, et al., "Evaluation of photon-counting spectral breast tomosynthesis", Medical Imaging 2011: Physics of Medical Imaging, vol. 7961, No. 1, Mar. 3, 2011.
(Continued)

*Primary Examiner* — Jose Couso

(57) ABSTRACT

A method for processing X-ray image data comprises: receiving sum image data (28) and difference image data (30), wherein the sum image data (28) and the difference image data (30) comprise intensity information of X-rays (18) of two different energies passing through an object (20), the sum image data (28) is based on a sum intensity of the two different energies and the difference image data (30) is based on a difference intensity of the two different energies; partitioning the difference image data (30) into a low frequency range (32) and a high frequency range (34); and generating low noise image data (36) by replacing the high frequency range (32) of the difference image (30) with a high frequency range based on the sum image data (28).

20 Claims, 3 Drawing Sheets

(51) Int. Cl.
  *A61B 6/00* (2006.01)
  *G06T 5/50* (2006.01)
  *G06K 9/62* (2006.01)

(52) U.S. Cl.
  CPC .............. *G06K 9/6215* (2013.01); *G06T 5/50*
  (2013.01); *A61B 6/502* (2013.01); *G01N*
  *2223/423* (2013.01); *G06T 2207/10116*
  (2013.01); *G06T 2207/20212* (2013.01); *G06T*
  *2207/20224* (2013.01); *G06T 2207/30068*
  (2013.01); *G06T 2211/408* (2013.01)

(58) Field of Classification Search
  CPC ......... G06T 5/001; G06T 5/002; G06T 5/007;
  G06T 5/008; G06T 5/009; G06T 7/12;
  G06T 7/38; G06T 2207/10081; G06T
  2207/30004; G06T 2207/10112; G06T
  2207/20016; G06T 2207/20012; G06T
  2207/20032; G06T 2207/20064; G06T
  2207/20221; G06T 2207/30068; G06T
  2207/10136; G06T 2207/10116; G06T
  2211/40; A61B 6/482; A61B 6/502; A61B
  6/5258; A61B 6/5235; A61B 6/032; A61B
  6/037; A61B 6/5247; A61B 6/484; A61B
  6/485; A61B 8/0825; A61B 8/4416;
  G01N 23/046; G01N 2223/419; G06K
  9/6215; G06K 7/1099; G03C 5/16; H04N
  5/32; Y10S 128/922; Y10S 378/901
  See application file for complete search history.

(56) References Cited

U.S. PATENT DOCUMENTS

| | | | | |
|---|---|---|---|---|
| 6,016,356 A | * | 1/2000 | Ito | G06T 5/004 |
| | | | | 382/132 |
| 6,683,934 B1 | * | 1/2004 | Zhao | A61B 6/032 |
| | | | | 378/37 |
| 8,391,576 B2 | * | 3/2013 | Kitamura | G06K 9/54 |
| | | | | 382/128 |
| 8,428,324 B2 | | 4/2013 | Heinlein | |
| 8,577,110 B2 | * | 11/2013 | Kitamura | G06T 5/50 |
| | | | | 382/128 |
| 8,639,003 B2 | * | 1/2014 | Bruder | G06T 5/002 |
| | | | | 382/131 |
| 8,792,617 B2 | * | 7/2014 | Baetz | A61B 6/4035 |
| | | | | 378/16 |
| 2008/0234578 A1 | | 9/2008 | Claus | |
| 2010/0061654 A1 | * | 3/2010 | Manak | G06T 5/50 |
| | | | | 382/275 |
| 2010/0166277 A1 | | 7/2010 | Raupach | |
| 2014/0169520 A1 | * | 6/2014 | Langan | G01N 23/046 |
| | | | | 378/5 |
| 2014/0185759 A1 | * | 7/2014 | Kang | G01N 23/04 |
| | | | | 378/62 |
| 2015/0348289 A1 | * | 12/2015 | Ida | A61B 6/032 |
| | | | | 382/131 |

OTHER PUBLICATIONS

Wataru Ito, et al., "Improvement of detection in computed radiography by new single-exposure dual-energy subtraction", Image Processing: Medical Imaging VI; vol. 1652, Feb. 24, 1992.

Fredenberg, et al., "Contrast-enhanced spectral mammography with a photon-counting detector", Medical Physics, vol. 37, No. 5, Apr. 12, 2010.

Oh, et al., "High contrast soft tissue imaging based on multi-energy X-ray", Medical Imaging 2011; vol. 7961.

* cited by examiner

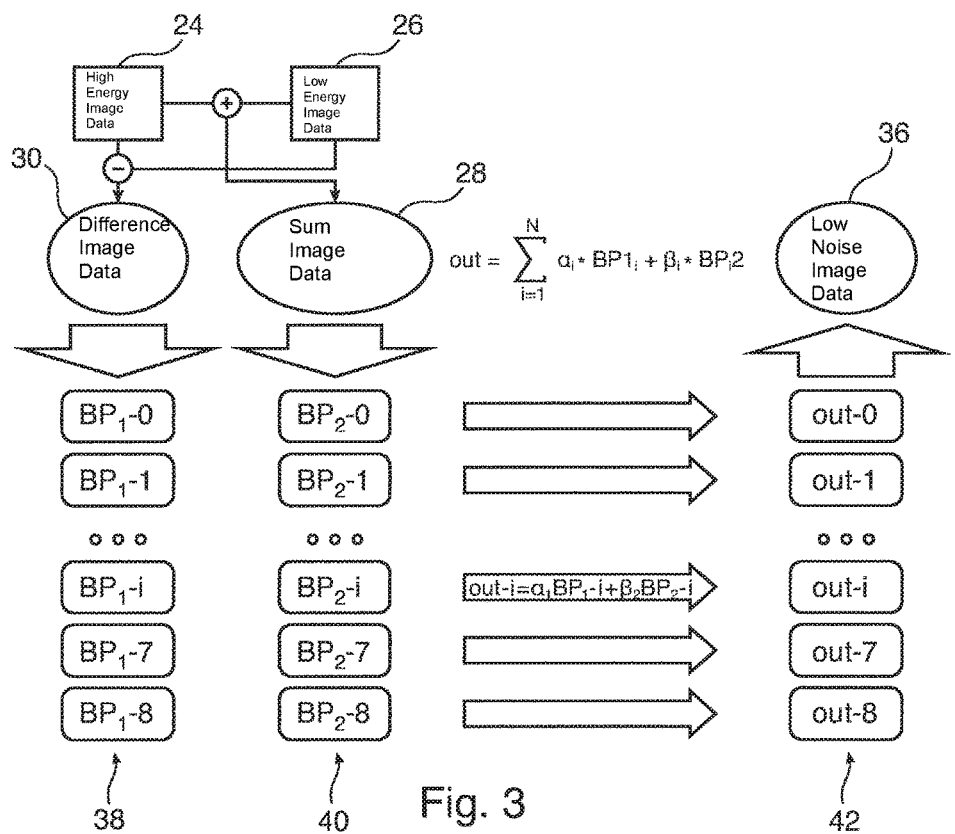
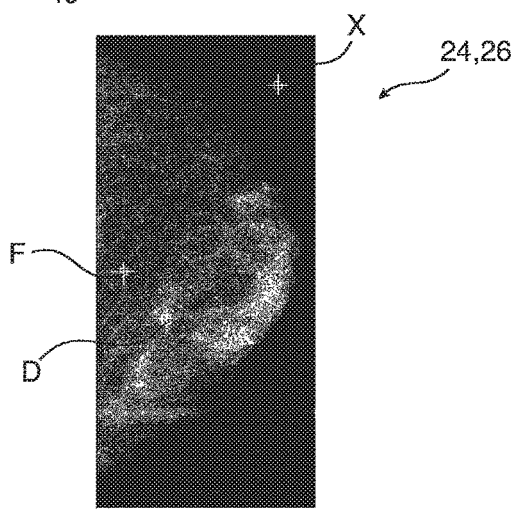
Fig. 4

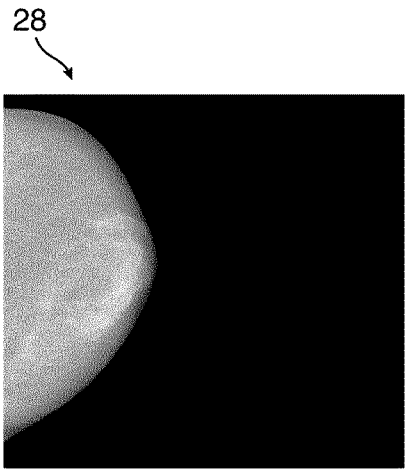 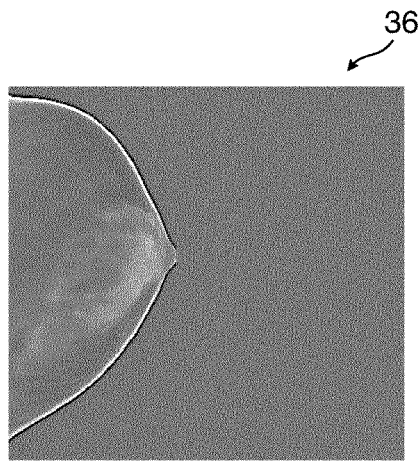
Fig. 5A  Fig. 5B
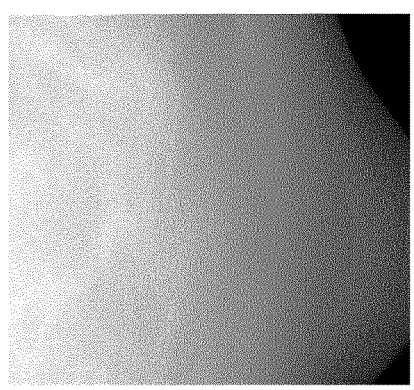 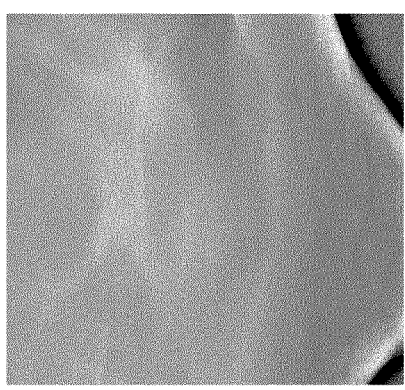
Fig. 6A  Fig. 6B
 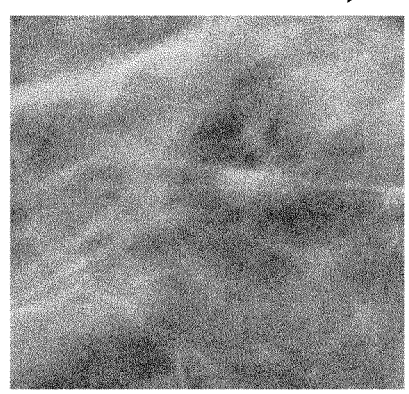
Fig. 7A  Fig. 7B

PROCESSING DUAL ENERGY SPECTRAL MAMMOGRAPHY IMAGES

CROSS REFERENCE TO RELATED APPLICATIONS

This application is the U.S. National Phase application under 35 U.S.C. § 371 of International Application No. PCT/EP2014/074298, filed Nov 12, 2014, published as WO 2015/074916 on May 28, 2015, which claims the benefit of European Patent Application Number 13193661.9 filed Nov 20, 2013. These applications are hereby incorporated by reference herein.

FIELD OF THE INVENTION

The invention relates to a method, a computer program and a computer-readable medium for processing X-ray image data. Furthermore, the invention relates to an X-ray imaging device.

BACKGROUND OF THE INVENTION

In the technology of X-ray dual energy, it is known to calculate specific images from the original energy images. In general, two X-ray images acquired at different X-ray energies are merged into one image. For example, the lung and the bones of the chest may be differentiated from each other with chest dual energy imaging.

For a dual energy soft tissue image, the two images acquired at different energies are subtracted using a scaling factor for the low energy image. What is visible in this soft tissue image is the structure of the lung vessels before the air background in the lungs because here the path through the tissue penetrates less tissue. The ribs are not visible in this image, so the added value of this image is that soft tissue structures like cancer nodules will bot be obscured by superimposed ribs, allowing a better detection.

For a dual energy bones image, the two images are subtracted from each other. The weight factor applied to the LOW image is different to the one used for the soft tissue image. When choosing the weight coefficients for the subtraction carefully, nearly only bones are visible and all soft tissue may be depicted with the same dark grey as the direct radiation next to the patient.

In spectral mammography, a mammography device is employed that comprises an X-ray detector that is adapted for differentiating X-rays of different energies. For example, WO 2013/076662 A1 discusses a type of spectral image processing.

SUMMARY OF THE INVENTION

The image types of chest dual energy imaging also may be used in spectral mammography. In Mammography, the "fatty tissue" may be seen equivalent to the soft tissue in chest imaging. The glandular tissue, which is embedded in the fatty tissue of the breast, may be seen equivalent to the bones in chest imaging. As the dense tissue is less transparent to X-ray than fatty tissue, it is often also called "dense tissue".

For a spectral mammography glandular image (or in general difference image), the two images of different energies are subtracted from each other in the log domain, using a scaling factor for the low energy image. This image may be seen analogously to the dual energy bone image. The location with dominating fatty tissue are shown as dark as the direct radiation. All tissue which is different from fatty tissue is shown bright.

As the glandular image usually is very noisy, there may be a need for reducing the noise in such type of image.

Such a need may be met by the subject-matter of the independent claims. Further embodiments of the invention are evident from the dependent claims and the following description.

An aspect of the invention relates to a method for processing X-ray image data, which may be seen as a method for providing low noise image data or spectral tissue image data that may be displayed as a further possible image during spectral mammography.

According to an embodiment of the invention, the method comprises the steps of receiving sum image data and difference image data, wherein the sum image data and the difference image data comprise intensity information of X-rays of two different energies passing through an object, the sum image data is based on a sum intensity of the two different energies and the difference image data is based on a (for example logarithmic) difference intensity of the two different energies; partitioning the difference image data into a low frequency range and a high frequency range; and generating low noise image data by replacing the high frequency range of the difference image with a high frequency range based on the sum image data.

The sum image data and/or the difference image data may be acquired by a detector of an X-ray mammography device that is adapted to differentiate between X-rays of different energies. It is also possible that the X-ray mammography device may acquire (first) low energy image data and (second) high energy image data and that the intensities of these two sets of data may be (pixel-wise) subtracted and added (possible with suitable weights) to form sum image data and difference (glandular) image data. Alternatively or additionally the X-ray mammography device may acquire the sum image data and the low energy image data and the other types of image data may be calculated therefrom.

In the end, a modified glandular image that does not show the enhanced noise or at least fewer noise, may be generated by replacing high spatial frequencies of the glandular image data by the properly scaled original information from the non-spectral sum image data.

In particular, the sum image data may be defined in a linear space (i.e. may contain information of the sum of intensities of low and high energy X-rays) and the sum image may be defined by the sum of the logarithm of the intensities of the values of the first image and second image. On the other hand, the difference image may be defined on the differences of the logarithm of the intensities of the low and high energy X-rays.

According to an embodiment of the invention, the sum image data is also partitioned into at a low frequency range and a high frequency range and the high frequency range of the difference image is replaced with a weighted sum of the high frequency ranges of the difference image data and the sum image data with the high frequency range of the sum image data weighted by a scaling factor. For example, the high frequency components of the difference image data/or and the sum image data may be extracted by Fourier transformation or with a Laplace pyramid and replaced in the difference image.

The generated low noise image may comprise the benefits of both image types. Small structures and noise may be as good as in the sum image. There may be no gradient towards a skin-line (border of the object/breast) as in the sum image.

The local brightness of the low noise image may be a measure for the amount of glandular tissue as in the difference image. In general, when displayed, the low noise image data may show only the relevant structures of the dense tissue in the breast with the non-relevant fatty tissue being quite transparent.

Further aspects of the invention relate to a computer program, which, when being executed by a processor, is adapted for performing the steps of the method as described in the above and in the following, and a computer-readable medium, on which such a computer program is stored. A computer-readable medium may be a floppy disk, a hard disk, an USB (Universal Serial Bus) storage device, a RAM (Random Access Memory), a ROM (Read Only Memory), an EPROM (Erasable Programmable Read Only Memory) or a FLASH memory. A computer-readable medium may also be a data communication network, e.g. the Internet, which allows downloading a program code.

A further aspect of the invention relates to an X-ray imaging device, for example a (spectral) mammography device comprising a detector arrangement for acquiring first and second image data relating to different X-ray energies; a controller for performing the method as described in the above and in the following and a display for displaying the low noise difference image.

It has to be understood that features of the X-ray imaging device as described in the above and in the following may be features of the method, computer program and the computer-readable medium as described in the above and in the following as well as vice versa.

These and other aspects of the invention will be apparent from and elucidated with reference to the embodiments described hereinafter.

BRIEF DESCRIPTION OF THE DRAWINGS

Below, embodiments of the present invention are described in more detail with reference to the attached drawings.

FIG. 3 shows a block diagram illustrating a method for processing image data according to an embodiment of the invention.

FIG. 4 shows an image illustrating specific points for determining weight factors for the method of FIG. 3.

FIGS. 5A, 6A, and 7A show sum images.

FIGS. 5B, 6B, and 7B show low noise images determined with a method for processing image data according to an embodiment of the invention.

The reference symbols used in the drawings, and their meanings, are listed in summary form in the list of reference signs. In principle, identical parts are provided with the same reference symbols in the figures.

DETAILED DESCRIPTION OF EMBODIMENTS

Figure 1:
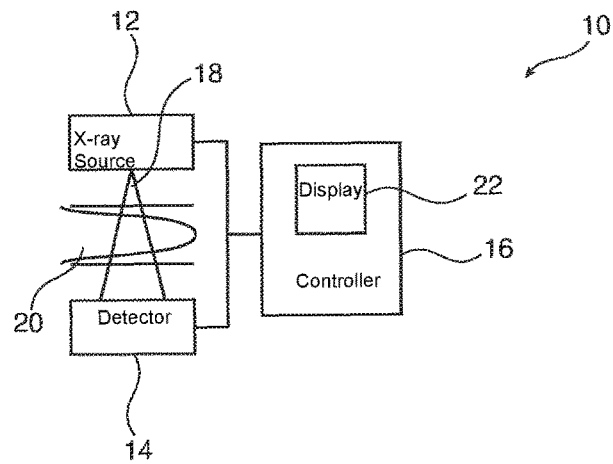
FIG. 1 schematically shows an X-ray imaging device according to an embodiment of the invention.

FIG. 1 schematically shows an X-ray imaging device 10, in particular a (spectral) mammography device 10 comprising an X-ray source 12, a detector 14 and a controller 16. When activated by the controller 16, the X-ray source 12 generates an X-ray beam 18 comprising quanta of different energies (as is usually the case with an X-ray rube). The X-ray tube passes an object 20 (such as a breast) and is attenuated. In particular, X-rays of different energies are attenuated differently.

The detector 14 is adapted for differentiating between X-rays of different energizes. For example, the detector 14 may count quanta about threshold energy and quanta below the threshold energy separately from each other. The projection of the X-ray beam through the object 20 is two-dimensional and according two-dimensional image data may be generated from the counted quanta in the controller 16. The detected quanta counted in separate channels may be identified as having either low or high energy and high energy image data and low energy image data may be generated.

It has to be understood that image data may be data that may be displayed as an image on a display 22, for example a display 22 of the device 10. Image data may comprise a plurality of pixels, wherein each pixel has an intensity and a position.

Figure 2:
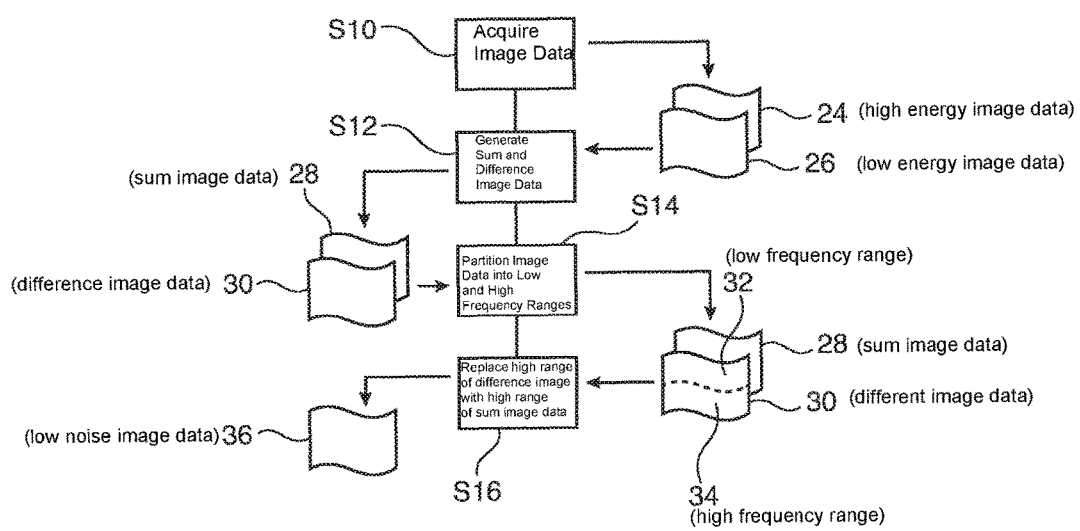
FIG. 2 shows a flow diagram for a method for processing image data according to an embodiment of the invention.

FIG. 2 shows a flow diagram for a method that may be performed by the controller 16, which may comprise a processor for executing a corresponding computer program.

In step S10, image data 24, 26 is acquired with the detector 14. With an accordingly adapted detector 14, first (low energy) image data 24 and second (high energy) image data 26 may be acquired (for example simultaneously). It has to be understood that in general the low energy image data 24 may relate to image data acquired at a lower X-ray energy as high energy image data.

For example, the low energy image data 24 may comprise intensity information of X-rays below a threshold value and the second image data 26 may comprise intensity information of X-rays above the threshold value. These types of image data may be acquired with a detector with two types of bins collecting quanta below and above the threshold value such as low and high channels of a spectral Mammography device.

However, the two sets of image data also may be acquired one after the other, wherein the X-ray source 12 is adjusted to different energies.

In the end, the controller 16 receives the first image data 24 and the second image data 26, wherein the first image data and the second image data comprise intensity information of X-rays 18 passing through the object 20 and the first image data relates to a different X-ray energy as the second image data.

In step S12, the controller 16 further processes the image data 24, 26 for generating sum image data 28 and difference image data 30.

The sum image data 28 is generated by calculating a sum of the first image data and the second image data, for example with the pixel-wise calculation:

$$\text{LOG [Sum]} = \text{LOG [High} + we \ast \text{Low]}$$

wherein High is the intensity of a pixel of the high energy image data, Low is the intensity of a pixel at the same position in the low energy image data 26, we is an energy weighting (that may be 1 and that is optional) and Sum is the intensity of the sum image data 28 at the same pixel, without a scaling with a logarithm. For the further steps below, a logarithm function is applied to the Sum value, which transforms the intensity value (scaling with energy) into a height value (scaling with attenuation) of the corresponding tissue. Summarized, the sum image data 28 is based on a logarithm of a (weighted) sum of the intensity values High and Low.

Furthermore in step 12, the difference image data 30 is generated by calculating a difference of the first image data 24 and the second image data 26, for example, with the pixel-wise formula Glandular=log(High)−wg*log(Low)

wherein wg is a further weighting and Glandular is the value of the difference image data at the corresponding pixel. The difference image data 30 is based on a (weighted) difference of logarithms of intensity values.

In the case of mammography, the resulting difference image data 30 may also be seen as glandularity image data, and may result in a cancellation image, in which the background signal is the fatty signal.

However, the glandularity image data 30 usually is very noisy and the following steps provide a modification. In general, in the following steps, a combination of the low-frequency component of the glandularity image data 30 with the high-frequency component of the logarithmic sum image data 28 is performed.

In step S14, the sum image data 28 and the difference image data 30 are both partitioned 30 into a low frequency range 32 and a high frequency range 34. For example, the difference image data 30 and the sum image data 28 are partitioned into frequency ranges 32, 34 by Fourier transforming the image data 28, 30 and selecting the respective ranges below and above a frequency value that is selected for removing the noise from the difference image data 30.

However, it is also possible to partition the difference image data 30 and the sum image data 28 into frequency bands by determining a Laplace pyramid of each of the sum image data and difference image data and to select the high frequency ranges 34 as the at least two or more highest frequency bands. This will be described below with respect to FIG. 3.

In step S16, the low noise image data 36 is generated by replacing the high frequency range 32 of the difference image 30 with a modified high frequency range based on the sum image data 28 and optionally the difference image data 30. The calculating may be represented by the following (simplified) formula:

low noise image=$cqf$*low_frequencies[difference image]+high_frequencies[LOG [sum image]]

wherein cqf is a weighting factor (which may be 1).

For example, after a Fourier transform, the components of the difference image data 28 below the threshold value may be composed with the components of the sum image above the threshold value and the result may be transformed with an inverse Fourier transform to form the low noise image 36.

The corresponding calculation with respect to the Laplace pyramid will be described with respect to FIG. 3.

Summarized, a modified version of the difference image or glandularity image ("Spectral tissue image") is generated, where the high spatial frequencies are taken from the logarithmized sum image and only the low spatial frequencies are taken from the glandularity image. The new image may be made by replacing the high spatial frequencies of a glandular type image by properly scaled original information from a non-spectral sum-image.

In the end, the low noise image data may be displayed on the display 22, for example to a radiologist, which then has direct visual access to the spectral information contained in the low energy and high energy image data 24, 26.

FIG. 3 shows a diagram illustrating the method of FIG. 2 in the case of decomposing the frequency content of the image data 28, 30 with a Laplace pyramid.

For the sum image data 28, a sum Laplace pyramid 38 is built, for example from the log(Sum) values. For the difference image data 30, a difference Laplace pyramid 30 is built, for example from the Glandular values. This results in a number of frequency bands $BP_1$-0 to $BP_1$-n for the difference image data 30 and an equal number of frequency bands $BP_2$-0 to $BP_2$-n for the sum image data 28. The number n may be 8.

In general, the frequency bands out-0 to out-8 of the low noise image data 36 are calculated from a weighted sum of the frequency bands of the difference image data 30 (weighted with a) and the frequency of the sum image data 28 (weighted with $\beta_i$). The low noise image 36 is formed by transforming the Laplace pyramid 42 back to an image.

One simple possible combination of weighting parameters is:

$\alpha_0=\alpha_1=\alpha_2=\alpha_3=0$; all other$\alpha$=cqf (ignore noise in 30 and scale fine structures from 30)
$\beta_0=\beta_1=\beta_2=\beta_3=1$; all other$\beta$=0 (copy highest bands)

In words, replace the (four) highest noisy bands of the difference image data 30 by the corresponding bands of the sum image data 29. Furthermore, rescale the other bands of the difference image 30, which is encoded in the factor cqf (see below). After that, low noise image=$(BP2-0+ \ldots +BP2-3)+cqf(BP1-4+ \ldots +BP1-n)$ With respect to FIG. 4, examples are given how the weighting factors wg and cqf may be determined. FIG. 4 represents both the high and low energy image data 24, 26.

As indicated in FIG. 4, F refers to a local average in the fatty (dark) part of the image data 24, 26, D refers to a local average in the dense (bright) part of the image data 24, 26, and X refers to a local average in the direct radiation (black).

Let FL be the fatty signal in the Low energy image data 24, FH be the fatty signal in the High energy image data 26, XL be the direct radiation in the Low energy image data 24 and XH be the direct radiation in the High energy image data 26. The sum values are calculated as follows

|  | sum | High Energy | Low Energy |
|---|---|---|---|
| signal x0 | XS | XH | XL |
| signal fatty | FS | FH | FL |
| signal dense | DS | DH | DS | and the factor wg is calculated from these values according to $wg=[\log(XH)-\log(FH)]/[\log(XL)-\log(FL)]$ Following this approach, no spectral system calibration is necessary.

The factor wg may also be derived from the absorption parameters μ, from the different materials in the two energy channels:

$wg=\mu_{fatty\_high}/\mu_{fatty\_low}$

From the above determined values, also the contrast quotient factor cqf of sum image and glandularity image may be determined:

$cqf=[\log(FS)-\log(DS)]/[\log(FH)-\log(DH)-wg*\{\text{Log}(FL))+\text{Log}(DL)\}]$ For the image shown cqf=−5.5.

These values can be measured in a proper system calibration using test phantoms.

With respect to FIG. 5A to 7B, a comparison of sum images 28 and low noise images 36 is provided. (In particular, the sum image shown is the log(sum) image. The low noise image is in the log-domain anyway.) The low noise image 36 shown in FIG. 5B (based on the low noise image data) shows the details better than the normal sum image 28 of FIG. 5A. It may be seen as a spectral image.

FIGS. 6A and 6B show cutouts from FIGS. 5A and 5B at the skinline. In this part of the image, one sees that the sum image 28 has a strong gradient at the skinline and it is difficult to display this adequately. The low noise image 30 is quite flat here.

FIGS. 7A and 7B show cutouts from FIGS. 5A and 5B from the inner part of the breast remote from the skinline. This part of the image is displayed with a comparable window setting for the two images. Therefore, the images 28, 36 look quite alike to each other, proofing that the image information is compatible.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

LIST OF REFERENCE SIGNS:

10 X-ray imaging device
12 X-ray source
14 X-ray detector
16 controller
18 X-ray beam
20 object (breast)
22 display
24 high energy image data
26 low energy image data
28 sum image data
30 difference image data
32 low frequency range
34 high frequency range
36 low noise image data
38, 40, 42 Laplace pyramid

The invention claimed is:

1. A non-transitory computer readable medium storing instructions executable by at least one electronic processor to perform a method for processing X-ray image data, the method comprising:
receiving sum image data and difference image data, wherein the sum image data and the difference image data comprise intensity information of X-rays of two different energies passing through an object, the sum image data is based on a sum intensity of the two different energies and the difference image data is based on a difference intensity of the two different energies;
partitioning the sum image data into a low frequency range and a high frequency range;
partitioning the difference image data into a low frequency range and a high frequency range, the low frequency range of the difference image data being weighted by a scaling factor;
generating low noise image data by replacing the high frequency range of the difference image with the high frequency range of the sum image data; and
control a display device to display the low noise difference imaging data.

2. The non-transitory computer readable medium of claim 1, further comprising:
operating a X-ray imaging device comprising an X-ray tube and an X-ray detector to acquire at least one of first image data and second image data, wherein the first image data and the second image data comprise intensity information of X-rays passing through an object and the first image data relates to a different X-ray energy as the second image data; and
at least one of:
generating the sum image data by calculate a sum of the first image data and the second image data; and
generating the difference image data by calculating a difference of the first image data and the second image data.

3. The non-transitory computer readable medium of claim 1, wherein the difference image data and the sum image data are partitioned into frequency ranges by a Fourier transform.

4. The non-transitory computer readable medium of claim 1, wherein the difference image data and the sum image data are partitioned into frequency bands by determining a Laplace pyramid of each of the sum image data and difference image data;
wherein the high frequency ranges comprise at least two highest frequency bands.

5. The non-transitory computer readable medium of claim 1, wherein at least one of:
the sum image data is based on pixel-wise adding intensity values of corresponding pixels of the first image data and second image data; and
the difference image data is based on pixel-wise subtracting intensity values of the corresponding pixels.

6. The non-transitory computer readable medium of claim 1, wherein at least one of:
the sum image data is based on a logarithm of a sum of intensity values; and
the difference image data is based on a difference of logarithms of intensity values.

7. The non-transitory computer readable medium method of claim 1,
wherein the first image data comprises intensity information of X-rays below a threshold value and the second image data comprises intensity information of X-rays above the threshold value.

8. The non-transitory computer readable medium of claim 1,
wherein at least one of: the first image data, the second image data, the sum image data, the difference image data; and the low noise image data comprise two-dimensional pixel data.

9. The non-transitory computer readable medium of claim 1,
wherein the first image data and the second image data are acquired with a detector adapted for differentiating X-rays of different energy.

10. An X-ray imaging device, comprising:
an x-ray tube;
a detector arranged respective to the x-ray tube to acquire first image data and second image data relating to different X-ray energies;
a display device; and
a controller programmed to:
acquire sum image data and difference image data using the detector arrangement and the x-ray tube, wherein the sum image data and the difference image data comprise intensity information of X-rays of two different energies passing through an object, the sum image data is based on a sum intensity of the two different energies and the difference image data is based on a difference intensity of the two different energies;
partition the sum image data into a low frequency range and a high frequency range;
partition the difference image data into a low frequency range and a high frequency range, the low frequency range of the difference image data being weighted by a scaling factor;
generate low noise image data by replacing the high frequency range of the difference image with a high frequency range based on the sum image data; and
control the display device to display display the low noise difference image data.

11. The device of claim 10,
wherein the X-ray imaging device is a mammography device.

12. The imaging device of claim 10, wherein the controller is programmed to:
acquire at least one of first image data and second image data using the detector arrangement and the x-ray tube, wherein the first image data and the second image data comprise intensity information of X-rays passing through an object and the first image data relates to a different X-ray energy as the second image data; and at least one of:
generate the sum image data by calculating a sum of the first image data and the second image data; and
generate the difference image data by calculating a difference of the first image data and the second image data.

13. The imaging device of claim 10, wherein the controller is programmed to:
partition the difference image data and the sum image data into frequency bands by determining a Laplace pyramid of each of the sum image data and difference image data;
wherein the high frequency ranges comprise at least two highest frequency bands.

14. The imaging device of claim 10, wherein the controller is programmed to at least one of:

pixel-wise adding intensity values of corresponding pixels of the first image data and second image data to generate the sum image data; and
pixel-wise subtracting intensity values of the corresponding pixels to generate the difference image.

15. The imaging device of claim 10, wherein the controller is programmed to at least one of:
generate a logarithm of a sum of intensity values to generate the sum image data; and
generate a difference of logarithms of intensity values to generate the difference image data.

16. The imaging device of claim 10, wherein the first image data comprises intensity information of X-rays below a threshold value and the second image data comprises intensity information of X-rays above the threshold value.

17. An X-ray imaging device, comprising:
a detector arrangement for acquiring first image data and second image data relating to first and second different X-ray energies;
a controller programmed to:
receive sum image data comprising a sum intensity of X-rays of the first and second different energies;
partition the sum image data into a low frequency range and a high frequency range;
receive difference image data comprising a difference intensity of X-rays of the first and second different energies;
partition the difference image data into a low frequency range and a high frequency range;
weight the low frequency range of the difference image data with a scaling factor;
generate low noise image data by replacing the high frequency range of the difference image with a high frequency range based on the sum image data;
control a display device to display the low noise difference image data.

18. The imaging device of claim 17, wherein the controller is programmed to:
calculate a sum of the first image data and the second image data; and
calculate a difference of the first image data and the second image data.

19. The imaging device of claim 17, wherein the controller is programmed to:
partition the difference image data and the sum image data into frequency bands by determining a Laplace pyramid of each of the sum image data and difference image data;
wherein the high frequency ranges comprise at least two highest frequency bands.

20. The imaging device of claim 17, wherein the controller is programmed to at least one of:
pixel-wise adding intensity values of corresponding pixels of the first image data and second image data to generate the sum image data; and
pixel-wise subtracting intensity values of the corresponding pixels to generate the difference image.

* * * * *